(12) United States Patent
Menzies et al.

(10) Patent No.: US 11,696,805 B2
(45) Date of Patent: Jul. 11, 2023

(54) DEVICE INTEROPERATION

(71) Applicant: CMR SURGICAL LIMITED, Cambridge (GB)

(72) Inventors: Rupert Menzies, Cambridge (GB); Paul Christopher Roberts, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 721 days.

(21) Appl. No.: 16/591,783

(22) Filed: Oct. 3, 2019

(65) Prior Publication Data

US 2020/0107897 A1 Apr. 9, 2020

(30) Foreign Application Priority Data

Oct. 3, 2018 (GB) ...................................... 1816165

(51) Int. Cl.
*A61B 34/37* (2016.01)
*B25J 9/16* (2006.01)
(Continued)

(52) U.S. Cl.
CPC ............. *A61B 34/37* (2016.02); *B25J 9/1697* (2013.01); *B25J 13/06* (2013.01); *G06F 21/44* (2013.01);
(Continued)

(58) Field of Classification Search
None
See application file for complete search history.

(56) References Cited

U.S. PATENT DOCUMENTS 9,283,675 B2 3/2016 Hager et al.
2016/0081753 A1* 3/2016 Kostrzewski .......... A61B 90/37
606/130
(Continued)

FOREIGN PATENT DOCUMENTS

EP 3537452 A1 9/2019
JP 2002272758 A 9/2002
(Continued)

OTHER PUBLICATIONS

Chilean Office Action from corresponding Chilean Application No. 202100821 dated Jun. 15, 2022.
(Continued)

*Primary Examiner* — Kristy A Haupt
(74) *Attorney, Agent, or Firm* — Lando & Anastasi, LLP

(57) ABSTRACT

A surgical robotic system comprising: a surgical robot; a user interface console coupled to the surgical robot whereby a user can control motion of the surgical robot; a data logger for logging data from a surgical procedure performed by means of the robot; and a portable user terminal; the system further comprising: a display controllable by one of the data logger and the user terminal, that one of the data logger and the user terminal being configured for displaying a machine-readable code whereby the data logger or a user of the user terminal can be identified; and a camera coupled to the other of the data logger and the user terminal; the said other of the data logger and the user terminal being configured to, on receiving from the camera an image of a machine-readable code, decode that code to identify the data logger or a user of the user terminal and to cause the identified entity to be logged in association with a procedure performed by means of the robot.

12 Claims, 2 Drawing Sheets

(51) Int. Cl.
   *B25J 13/06* (2006.01)
   *G06F 21/44* (2013.01)
   *A61B 34/00* (2016.01)
   *A61B 90/00* (2016.01)
   *A61B 90/50* (2016.01)
   *A61B 90/96* (2016.01)
   *A61B 5/117* (2016.01)
   *A61B 17/00* (2006.01)
   *G06F 21/31* (2013.01)
   *H04N 23/54* (2023.01)

(52) U.S. Cl.
   CPC ............... *A61B 5/117* (2013.01); *A61B 90/50* (2016.02); *A61B 90/96* (2016.02); *A61B 2017/00221* (2013.01); *A61B 2034/258* (2016.02); *A61B 2090/3612* (2016.02); *A61B 2090/373* (2016.02); *G05B 2219/40414* (2013.01); *G05B 2219/50391* (2013.01); *G06F 21/31* (2013.01); *H04N 23/54* (2023.01)

(56) References Cited

U.S. PATENT DOCUMENTS

| | | | |
|---|---|---|---|
| 2016/0314462 A1 | 10/2016 | Hong et al. | |
| 2016/0331474 A1* | 11/2016 | Lacal | A61B 34/35 |
| 2018/0168755 A1* | 6/2018 | Cagle | A61B 34/25 |

FOREIGN PATENT DOCUMENTS

| | | |
|---|---|---|
| JP | 2002366665 A | 12/2002 |
| JP | 2017503253 A | 1/2017 |
| JP | 2018515229 A | 6/2018 |
| RU | 2412800 C2 | 2/2011 |
| WO | 2018225121 A1 | 12/2018 |
| WO | 2019130096 A1 | 7/2019 |
| WO | 2020070505 A1 | 4/2020 |

OTHER PUBLICATIONS

Japanese Decision to Grant a Patent from corresponding Japanese Patent Application No. 2021 518572 dated Sep. 30, 2022.
United Kingdom Combined Search and Examination Report from corresponding United Kingdom Application No. GB2212193.3 dated Oct. 13, 2022.
United Kingdom Search Report from corresponding United Kingdom Application No. GB1816165.3 dated Mar. 28, 2019.
Notification of Transmittal of the International Search Report and Written Opinion of the International Searching Authority from corresponding PCT/GB2019/052796 dated Dec. 20, 2019.
Japanese Notification of Reasons for Refusal from corresponding Japanese Patent Application No. 2021-518572 dated May 2, 2022.
Russian Decision to Grant from corresponding Russian Application No. 20221505032 dated Mar. 23, 2023.

* cited by examiner

DEVICE INTEROPERATION

CROSS-REFERENCE TO RELATED APPLICATION

This application claims the benefit under 35 U.S.C. § 119 of United Kingdom Patent Application No. 1816165.3 filed on Oct. 3, 2018 which is hereby incorporated herein by reference in its entirety for all purposes.

This invention relates to interoperating devices. The devices could, for example, collect and distribute information concerning robotic surgical procedures.

Surgical robots are used to perform medical procedures on humans or animals. A surgical robot typically comprises a moveable mechanism (robot arm) which supports an end effector which is a surgical instrument. The mechanism can be reconfigured to move the end effector to a surgical site and to operate the end effector to perform surgery. The robot is typically controlled by a surgeon operating a console which is communicatively coupled to the robot, and partially or fully automated surgery has also been envisaged.

One potential advantage for robotic surgery over conventional manual surgery is that it permits data to be gathered more easily about how surgical procedures are performed. The motion of the robot during the surgery can be monitored and logged and compared with what happened in previous procedures to help identify process improvements. To achieve this, it would be desirable for the system to know which staff were involved in a particular procedure.

In principle, high volumes of data on surgical procedures could be collected in an automated way and stored and distributed to interested parties. However, if this were to be done without sufficient technical safeguards then there is a risk that the collected data could come into the possession of unauthorised parties. There is a need for security measures for inhibiting the loss of sensitive surgical data collected in this way.

According to one aspect there is provided: a surgical robotic system comprising: a surgical robot; a user interface console coupled to the surgical robot whereby a user can control motion of the surgical robot; a data logger for logging data from a surgical procedure performed by means of the robot; and a portable user terminal; the system further comprising: a display controllable by one of the data logger and the user terminal, that one of the data logger and the user terminal being configured for displaying a machine-readable code whereby the data logger or a user of the user terminal can be identified; and a camera coupled to the other of the data logger and the user terminal; the said other of the data logger and the user terminal being configured to, on receiving from the camera an image of a machine-readable code, decode that code to identify the data logger or a user of the user terminal and to cause the identified entity to be logged in association with a procedure performed by means of the robot.

The surgical robot may comprise a robot arm having a surgical instrument attached thereto as an end effector of the arm.

The camera may be coupled to the data logger.

The surgical robot may be located in an operating room. The camera may be positioned such that its field of view extends into the operating room.

The camera may be located outside the operating room.

The portable user terminal may be configured to locally generate the machine-readable code as a function of an identity of a user using the terminal.

The portable user terminal may be configured to locally generate the machine-readable code as a function of a current time.

The portable user terminal may be configured to locally generate the machine-readable code so as to include data whereby the code can be authenticated to the portable user terminal.

The data logger may be configured to, on receiving from the camera an image of a machine-readable code, determine whether that code is authenticated to a portable user terminal and if that determination is negative to not log the identity of any user identified by the code in association with a procedure performed by means of the robot.

The data logger may be configured to, on receiving from the camera an image of a machine-readable code, determine a time indicated by the code and if that time is more than a predetermined time before the current time to not log the identity of any user identified by the code in association with a procedure performed by means of the robot.

The camera may be coupled to the portable user terminal.

The data logger may be configured to generate the machine-readable code as a function of one or more of (i) an identity the data logger, (ii) an identity of robotic equipment functionally coupled to the data logger, (iii) an algorithm implemented by the data logger for generating a data unique to the data logger and (iv) current time.

The data logger may be configured to locally generate the machine-readable code so as to include data whereby the data logger can be authenticated to the portable user terminal.

The portable user terminal may be configured to, on receiving from the camera an image of a machine-readable code, determine whether that code authentically indicates a data logger and if that determination is positive to transmit data to cause the identity of a user associated with the terminal to be associated with a procedure performed by means of the robot.

According to a second aspect there is provided a method for analysing the performance of a surgical robotic system, the method comprising: performing a surgical procedure using a surgical robot; measuring, during the procedure, the state of the robot at multiple times; storing log data indicative of the measured state of the robot at the multiple times, and including an indication of a user involved in the procedure and their role in the procedure; storing a dataset defining a set of metrics, each metric defining one or more states of the surgical robot and indicating a role; applying one of the metrics to the stored log data by identifying the defined one or more states of the surgical robot in the log data and thereby deriving an indicator of performance of the surgical robot; and selectively reporting the indicator of performance to the user indicated by the log data as having had in the procedure the role indicated by the metric.

A metric may define an initial state of the surgical robot and a final state of the surgical robot, and the step of applying that metric to the stored data may comprise determining the time elapsed during the surgical procedure between the robot being in the first state and being in the second state.

The step of selectively reporting may comprise prioritising the reporting of the indicator of performance to the user indicated by the log data as having had in the procedure the role indicated by the metric.

The step of selectively reporting may comprise blocking the reporting of the indicator of performance to at least one user indicated by the log data as having had a role in the procedure other than the role indicated by the metric.

The step of applying may be performed at a server and the method may comprise the steps of: receiving the indicator of performance at a mobile user terminal associated with the user indicated by the log data as having had in the procedure the role indicated by the metric; and displaying the indicator of performance on the mobile user terminal.

The surgical procedure may be performed in an operating room and the method comprising the steps of: initiating the surgical procedure; subsequent to the initiating step, displaying on one of a mobile user terminal and a data logger a machine-readable code whereby the data logger or a user of the user terminal can be identified; capturing an image of the code by means of a camera coupled to the other of the data logger and the user terminal; and subsequent to the displaying step, terminating the procedure; analysing the code to determine the identity of the user or the data logger identified thereby; and (i) if the camera is coupled to the data logger: determining a role associated with the user identified by the code and storing the log data identifying that user as being involved in a procedure conducted by the data logger; or (ii) if the camera is coupled to the user terminal: determining a procedure performed by the data logger identified by the code and storing the log data identifying a user of the user terminal as being involved in that procedure.

The camera may be coupled to the data logger.

A role of the user may be indicated in the code.

The code could be generated as a function of the type of the procedure, for example as designated by a predetermined identity for that procedure.

The method may comprise storing a database mapping a plurality of users each to a respective role. The step of determining a role associated with the user may comprise looking up that user in the database and retrieving the role associated therewith.

The surgical procedure may be performed in an operating room and the method may comprise the steps of: initiating the surgical procedure; subsequent to the initiating step, displaying on a display unit installed in the operating room a machine-readable code identifying the procedure; capturing an image of the code by means of a mobile user terminal associated with a user; and subsequent to the displaying step, terminating the procedure; analysing the code to determine the identity of the procedure; determining a role associated with the user of the terminal; and in response to the capturing of an image of a code identifying the procedure by a mobile user terminal associated with that user at a time between the initiating and terminating steps, storing the log data indicating that user as being involved in the procedure and having the determined role.

The present invention will now be described by way of example with reference to the accompanying drawings.

In the drawings:

FIG. 1 shows a set of devices that are capable of interoperating to distribute information relating to the performance of a robotic procedure. In this case, that procedure is a surgical procedure.

Figure 1:
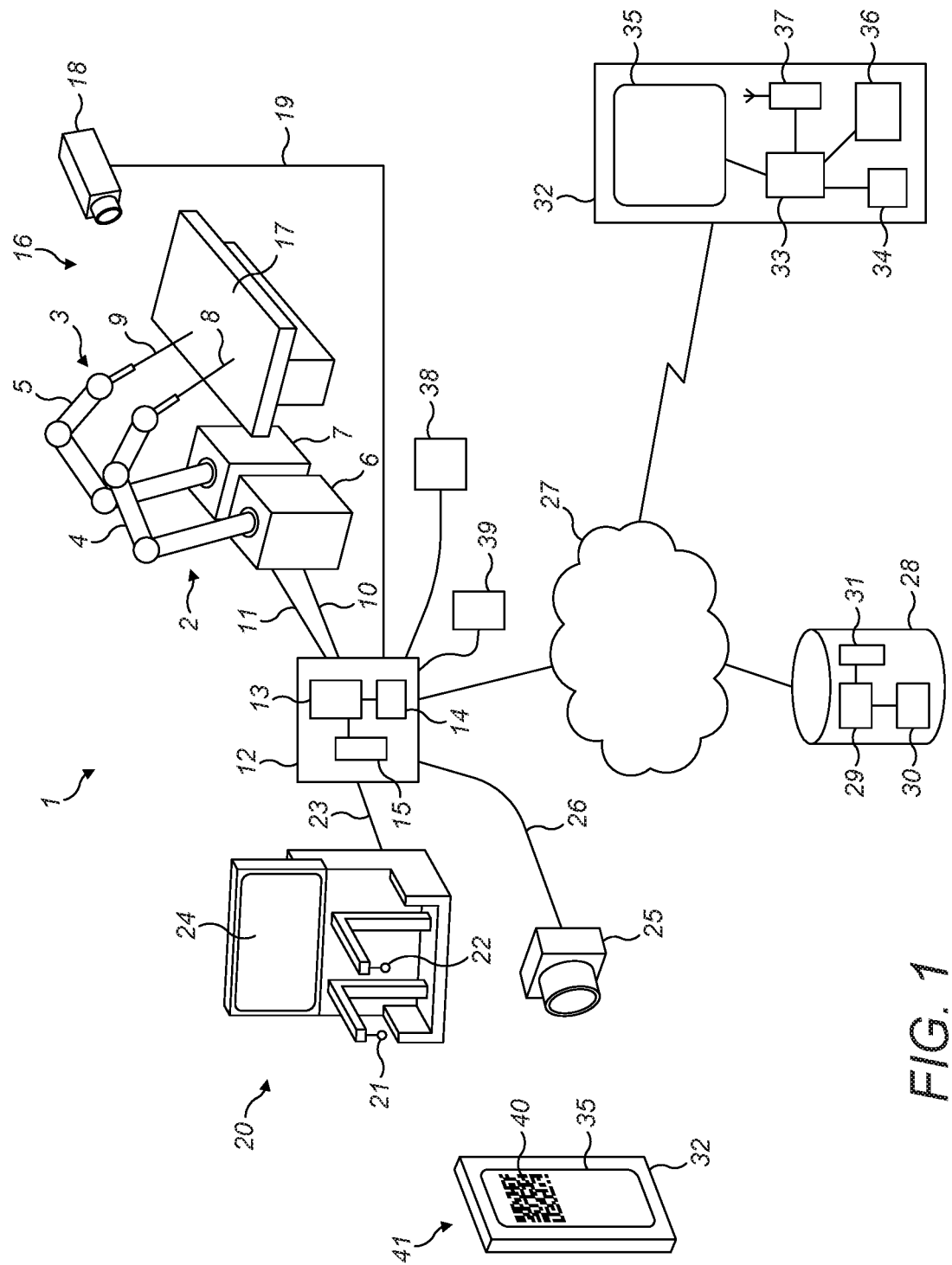
FIG. 1 shows a set of interoperating devices in which a user is identified by detecting a visible code displayed on a user terminal.

A surgical robot installation is shown generally at 1. The installation comprises two surgical robots 2, 3. Each surgical robot has a robot arm 4, 5 extending from a base 6, 7. Each arm comprises a series of rigid arm elements which are articulated with respect to each other and to the respective base by flexible joints. The joints are provided with drives such as motors or hydraulic actuators which can drive motion of the arms at their joints. Each arm terminates at its distal end in an end effector 8, 9. In this example, end effector 8 is a grasping tool and end effector 9 is an endoscope. The robots could be of any suitable design. Different end effectors could be used: for example cutting or irradiating tools.

A data link 10, 11 connects each robot communicatively to a control unit 12. The control unit comprises a processor 13 and a memory 14. The memory stores in a non-transient way code that is executable by the processor to enable the control unit to carry out its functions. The data links may be wired or wireless links. The data links 10, 11 carry signals from the control unit 12 to the robots to control the joint drives. The data links also carry signals from the robots to the control unit which convey data sensed by the arms. The sensed data may include images captured by endoscope 9. The sensed data may include information indicating the pose of the arms and/or forces acting on the arms, which may be gathered by position and/or force sensors on the arms. The control unit includes a cache memory 15 which can be used to store data gathered during a robotic procedure.

The robot arms are located in an operating room 16 having an operating table 17. A camera 18 is located in the operating room so as to have an overview of the robots' field of work. A data link 19 carries video data from the camera 18 to the control unit 12. Data link 19 may also carry data from the control unit 12 to the camera, for example to command the camera to move or zoom. The control unit 12 may be inside or outside the operating room 16; or some of its functions may be implemented inside the operating room 16 and some outside.

The surgical robot installation has a surgeon console 20. The surgeon console may be located in the operating room 16 or remotely from it. The surgeon console comprises inputs 21, 22 for controlling the state of arms 4, 5. In this example the inputs are handgrips mounted on parallelogram linkages equipped with position sensors for sensing the pose of the linkages. A data link 23 carries data from the console to the control unit 12 indicating the pose of the inputs, and any other information that may be signalled by an operator, for example by operating switches mounted on the handgrips. The surgeon console comprises a display 24. The display is arranged to be visible to a user operating the inputs 21, 22. The display displays a video stream transmitted from the control unit 12 over data link 23. The video stream may include video (e.g. from endoscope 9 or camera 18) and status information generated by the control unit 12.

A camera 25 is coupled to control unit 12 by data link 26. The function of this camera will be described further below. Camera 25 may be mounted within the operating room 16. Camera 25 may be mounted outside the operating room 16 but with a field of view inside the operating room. 16. Alternatively, camera 25 may be mounted entirely remotely from the operating room 16.

The control unit 12 is connected via a network 27 to a data server 28. The data server comprises a processor 29 and a memory 30. The memory stores in a non-transient way code that is executable by the processor to enable the data server to carry out its functions. The data server also has a cache memory 31 for storing information relating to historical robotic procedures.

A user terminal 32 is provided. The user terminal may, for example, be a smartphone, tablet, notebook or desktop computer. The user terminal comprises a processor 33 and a memory 34. The memory stores in a non-transient way code that is executable by the processor to enable the user terminal to carry out its functions. The user terminal also comprises a display 35 which can be controlled by the processor 33 to display information, an input device 36 by means of which a user can provide input to the processor and a communication interface 37. The input device may, for example, be a keypad or touchscreen membrane. The communication interface may be a wired or wireless communication interface. Conveniently the communication interface is a wireless communication interface that supports a cellular protocol and/or an IEEE 802.11b protocol. The communication interface 37 can connect to the network 27, and via that network to the server 28.

The operation of the system shown in FIG. 1 will now be described.

To perform a surgical procedure, a patient is brought into operating room 16 and laid on operating table 17 with the intended site of the procedure within the working range of the robots 2, 3. Appropriate end effectors are attached to the robots. Medical staff may be in the operating room to assist with the procedure. The processor 13 is configured to execute code to perform the following functions.

1. To receive from the surgeon console 20 information regarding the pose of the inputs 21, 22 and any other inputs from the surgeon console, and to control the joint drives of the robots 2, 3 in dependence on that information. This permits the surgeon to move the robot arms 4, 5 and to control their end effectors. To achieve this, the code stored in memory 14 may define a mapping between positions and/or poses of each input 21, 22 and positions and/or poses of a respective one of the arms 4, 5. When one of the inputs is moved, that is detected by the sensors on that input and information defining the new position and/or pose of the input is transmitted via data link 23 to the control unit 12. The control unit interprets that information and determines a corresponding target pose for the respective robot arm, or a target position for the end effector of the arm. The control unit determines which movements of which joints of the arm are required to achieve that position or pose, and then transmits signals over data link 10 or 11 to cause the joint drives of the appropriate arm to move the arm into the appropriate configuration to achieve that pose or position.

2. To receive data from the arms 2, 3, surgeon console 20, camera 18, camera 25 and any other data gathering units 38 associated with the robots or the operating room 16 and to store that data in cache memory 15. The data gathering units 38 may include patient monitors such as blood pressure monitors, pulse monitors, breathing monitors and the like. The data gathering units 38 may also include a microphone for gathering audio information from the operating room. The received data may, for example, be indicative of any one or more of the following: the pose of a robot arm or a part of it, a force or torque experienced on a component of a robot arm (e.g. the load on a joint of the arm, or the force experienced by an end effector of the arm), data gathered by a sensing end effector of the arm (e.g. a video feed from endoscope 9), a video feed from camera 18, inputs received from the surgeon consoles (e.g. the pose of the arms 21, 22, forces applied on those arms or any joints of those arms, the positions of the hand grips on those arms and any button presses or other inputs made on the surgeon console), and data from units 38 such as an audio feed from the operating room 16 and data on the vital signs of the patient.

3. To generate an output video feed to control display 24. The output video feed may include video from endoscope 9 and/or camera 18. These may be supplemented by signs such as text or graphics indicating the status of the robots 2, 3 and the patient. Once a surgical procedure has been completed, or whilst it is taking place, the control unit 12 transmits some or all of the data gathered through function 2 above, together optionally with (i) data defining inputs received from the surgeon console and (ii) other data determined by the control unit (e.g. target arm poses) to server 28. Processor 29 of server 28 stores the received data in cache memory 31.

The information on a particular procedure may be stored together with data indicating the context of the procedure. That context data may include any of: the identities of staff involved in performing the procedure, the roles of those staff, the identity of the patient on whom the procedure was performed, the nature of the procedure (which may include an indication of the region of the body on which the surgery was performed and optionally the technique used), the end effectors used in the procedure, the identity of any equipment used in the procedure (e.g. the serial numbers of the arms 4, 5 and any components of them), information indicating steps that were taken or equipment that was used prior to the performing of the procedure (e.g. any of: the patient's history, the patient's diagnosis, medical imaging of the patient, modelling of the patient and measurements conducted on the patient), information indicating one or more members of a team performing the procedure, the time and/or date when the procedure was performed, the duration of the procedure, and post-procedural outcomes (e.g. any of: outcomes of the procedure, complications of the procedure, follow-up treatment and lengths of hospital stay). Some or all of the above information may be stored by way of values stored in predetermined fields that can accept a limited number of inputs, e.g. yes/no flags. This can assist in subsequent analysis of the data that has been captured. The contextual information may be gathered by being entered at surgeon console 20 or at a computer terminal 39, at a console operated by another person, or it may be entered in an automated way as will be described below.

A user of device 32 can set up a user account with server 28. This may be done in the conventional way, by the user causing the device 32 to communicate with the server 28 and thereby establishing security credentials such as a user name and a password with which the user can authenticate to the server in future. The credentials, or a secure representation of them, are then stored by server 28 so that the user can be recognised in the future. The user may provide the server with additional information associated with their user account. That additional information may, for example, include any of: the user's name, a nickname, the place where the user works and the user's occupation or role. For example, in the case of a healthcare worker the user's account may include an indication that they are an operating theatre technician or a surgeon. The user terminal 32 may run a dedicated application that communicates with the server 28. Code defining that application may be stored in memory 34 for execution by processor 33. Alternatively, the user terminal 32 may communicate with the server by means of a generic communications application such as a web browser.

Some functions of the user terminal 32 will now be described.

A user of terminal 32 can log on to the server 28 and review information stored in memory 28 about previous procedures done by the robotic system 1. For example, the user can (i) download from memory 31 video data from endoscope 9 or camera 18 and view that on display 35 of the device or (ii) download from memory 31 information about the status of one or more of the robots 2, 3 or the patient on whom a procedure is being performed and display that on the device. The server may be configured so that the ability to download particular information from the server 28 is restricted to certain users or classes of users. For example, the ability to download information about a certain procedure may be restricted to users recorded in server 28 as having been staff involved in the procedure, or to users recorded in server 28 as being administrators of such staff.

As discussed above, in order for the system to identify which individuals have been involved in a surgical procedure, the identities of those individuals can be provided to control unit 12 by being entered in at the surgeon console 20 or a computer terminal 39. However, this approach has a number of problems. For example, the surgeon console 20 might not have a conventional keyboard, and it may be difficult to maintain hygiene if users in an operating room are expected to enter their credentials into computer terminal 39. Another approach to identifying the relevant individuals is for the individuals to provide input to their terminals 32 to indicate that they are about to be involved in a procedure, and for the terminals to transmit that to the control unit 12 either directly or via the server 28. A problem with this approach is that it is desirable that communications between the control unit 12 and network 27 are highly secure since the consequence of unauthorised access being gained to the control unit 12 are potentially severe. For maximum security, it is preferable that the control unit 12 does not accept any incoming traffic from network 27. That precludes the user identities being populated from server 28 or user terminal 32.

In the system of FIG. 1 it is possible for a user to identify themselves to control unit 12 by means of camera 25. One way in which this can be done is by the user controlling their terminal 32 to display an image that can be sensed by camera 25 and then decoded by control unit 12 to determine the user's identity. That image may be text or more preferably an array of high-contrast geometric shapes such as two-dimensional bar-code 40 shown on an instance 41 of user terminal 32 whose display 35 is directed to camera 25. In more detail, this identification process may function in the following way.

1. The control unit 12 is readied for the performance of a new robotic procedure.
2. A user of terminal 32 navigates a user interface of the terminal to cause it to display image 40.
3. Image 40 is shown to camera 25, which transmits the sensed image to control unit 12.
4. Processor 13 of control unit 12 executes code to decode the image and thereby identify an individual.
5. Processor 13 stores the identity of the individual in cache memory 15 in association with the procedure to be carried out.

The image may be generated at the terminal 32 using an algorithm defined by code stored in memory 34 or it may be downloaded by terminal 32 from server 28. The image may indicate the identity of the user and optionally a time stamp associated with the image. The time stamp may indicate a time when the image was generated or when the validity of the image expires. The control unit 12 may be configured to accept the image as valid input only during the period when the image is valid. The image may include validation data such as a checksum or a hash of other data represented in the image, so that the control unit 12 can verify that the image is valid. The validation data may define the result of a function such as a hash or a public/private key authentication or encryption algorithm. For example, a secret key may be transmitted to the user terminal by the server 28 and stored by the user terminal and the server. The validation data may include a hash of a subset of the data indicated by the image together with the secret key. The server can authenticate the user by checking the hash using the key it has stored. The validation data can be used to authenticate the identity of the user of the terminal and to verify that the user is entitled to access the system. The validation data can be augmented by a passcode entered on the user terminal. In this way it can further be authenticated that a particular user is in possession of the terminal. This can help to prevent someone impersonating another user. By displaying the user-identifying image on the user terminal at 41, and taking that as input via camera 25 the user can be identified to the system without the user touching terminal 39 and with incoming data from network 27 to control unit 12 blocked. The user may be in the operating room 16 when they show the code to the camera 25.

Figure 2:
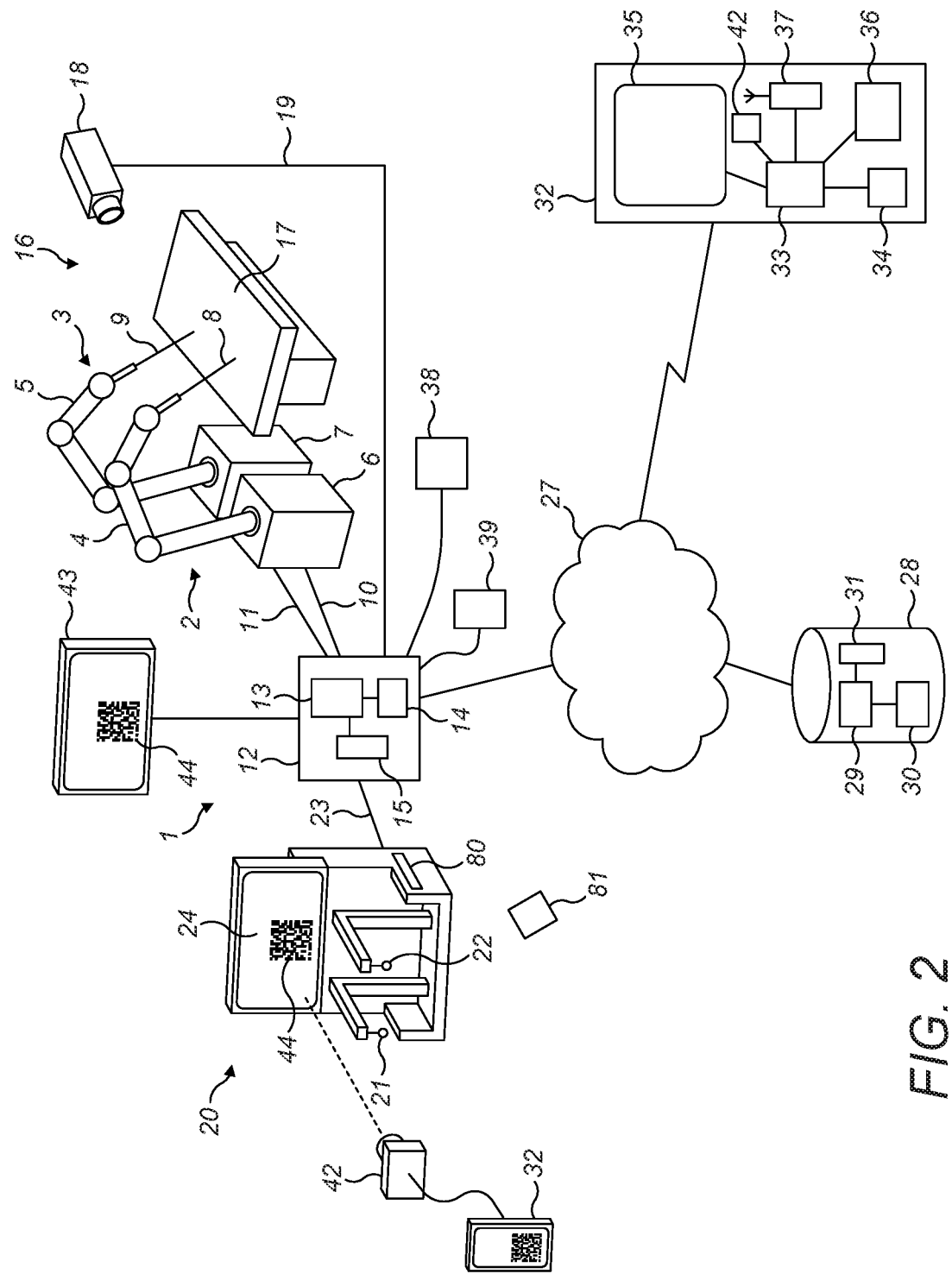
FIG. 2 shows a set of interoperating devices in which a user is identified by detecting a visible code using a user terminal.

Another way in which a user can be identified to the system is by the user controlling their terminal 32 to detect a machine-readable image. FIG. 2 shows a version of the system of FIG. 1 which supports this mode of operation. In FIG. 2 like parts are numbered as in FIG. 1. The user terminal 32 includes, or is connected to, a camera 42 which can capture images and pass them to processor 33. A video screen 43 is provided in on near the operating room 16. The video screen is controlled by the control unit 12. At the outset of a procedure the control unit 12 controls display 24 and/or display 43 to show an image. That image may be text or more preferably an array of high-contrast geometric shapes such as two-dimensional bar-code 44. That image can be sensed by camera 42 and passed to processor 33. Processor 33 may decode the image to determine data embedded within it. Processor 33 then causes the image or the decoded embedded data to be transmitted along with information identifying the user of the terminal 32 to the server 28. The server 28 can use that information to establish that the user of the terminal is about to be engaged in the procedure. One way in which the server 28 can determine that is if an identifier of the procedure is embedded in the image, and decoded from the image by processor 33 or server 28. Another way in which the server 28 can determine that is if the image is characteristic of the procedure (e.g. by having been randomly generated for the procedure by control unit 12) and then transmitted by control unit 12 to server 28 together with an indication of the procedure that image relates to. Another option is for the image to be characteristic of the procedure (e.g. by having been randomly generated for the procedure by server 28) and then transmitted by server 28 to control unit 12 in connection with the setting up of the procedure. The users of other terminals involved in the procedure can take similar steps to capture image 44 and thereby register for the procedure with server 28. In this way, server 28 can determine who was involved in the procedure. A user's role in the procedure may be designated by the user specifically in connection with that procedure, may be pre-stored at terminal 32 and transmitted to server 28 or may be pre-stored at server 28, e.g. in the user's account settings on the server.

After one or more robotic operating procedures have taken place, a user of the system who has sufficient rights can access information on those procedures using a user terminal 32. Some examples of how that access may take place are as follows.

1. The user may view images and/or video of the procedure. They may have been captured by endoscope 9 or camera 18. The images and/or video may be presented on the display 35 of the user terminal 32. The images and/or video may be presented together with data relating to the state of the robot equipment and/or the patient contemporaneously with the image or portion of video being viewed. That state information may be overlain on the image/video or displayed alongside it. The state information could, for example, include any one or more of: information indicating the position or pose of a robot arm, information identifying the type of end effector attached to a robot arm, information on the patient's vital signs and information indicating the time since the start of the procedure or an identifiable segment of it.

2. The user may view metrics generated by server 28 relating to an individual procedure or to multiple procedures. Examples of such metrics might include the total duration of the procedure, the number of end effector changes during the procedure and the total distance moved by the tip of the end effector of a robot during the procedure. These values can be calculated by the server 28 in dependence on the data provided to it by the control unit 12.

3. The server 28 may generate recommendations for the user in dependence on the data it holds about procedures the user has been involved in. The recommendations determined by the server may be dependent on the role of the user either as stored for their user account in server 28 or as indicated for a particular procedure. For example, if the user's role is as a surgeon then the terminal may receive from the server 28 and display information on techniques to improve suturing technique whereas if the user's role is as an anesthetist then the terminal may receive from the server 28 and display information comparing patient vital signs between past procedures.

4. The user may download data, e.g. video data, to terminal 32 directly from control unit 12 or terminal 20. This could be done through a wired or wireless connection between terminal 32 and control unit 12; or by the user causing control unit 12 to store the required data on a removable memory device 81 such as a memory stick, removing that from the server 12 or terminal 20 and mating it with terminal 32. Control unit 12 or terminal 20 may have a connector 80 for mating physically with the removable memory device and communicating with it to store data thereon.

The control unit 12 and/or the server 28 may store data indicating the identities of members of a surgical team who have participated in a procedure. After a procedure, the server 28 may make data relating to that procedure available to each of those participants or a subset of them. This may be achieved by a user accessing the server by means of an application running on their terminal 32, the server verifying the identity of the user, and the server then making available to that user through the application data concerning procedures in which that user has been indicated as having been involved. The data that is made available may be provided to the server 28 in a number of ways. In one approach, the data is transmitted to the server by the control unit 12 or terminal 20 over a data link via network 27. In another approach, the data can be stored by control unit 12 or terminal 20 on a removable data carrier 81 when the data carrier is physically connected to control unit 12 or terminal 20, for example in socket 80. The removable data carrier 81 can then be removed from its physical connection with the surgical equipment, and taken to a separate computer from which the data on it can be uploaded to server 28. This avoids the need for the surgical equipment to have a connection to network 27, or can reduce the amount of data that needs to be transmitted over such a connection, especially when the captured data includes video information. The data can be stored on the removable data carrier in encrypted form, and transmitted to the server 28 in that encrypted form, and then decrypted by the server 28.

To improve the quality of feedback on robotic procedures, the identities of staff involved in a procedure can be taken into account in analysis and/or reporting performed by the control unit 12 or the server 28. The control unit 12 or the server 28 may hold (e.g. in memory 15 or 30) role analysis data which associates specific user roles with respective performance characteristics of the robotic system. For example, from time to time during a surgical procedure it is necessary to change the instrument on an arm. The role analysis data may associate the time gap between the withdrawal of an instrument from a patient and the reinsertion of a different instrument attached to the same arm with a user who was fulfilling the surgical assistant role for that procedure. In another example, the role analysis data may associate the number of sutures performed during a procedure with a user fulfilling the surgeon role for that procedure. A processor such as 13 or 33 has access to the role analysis data together with (i) information ("A") indicating how one or more robotic procedures were performed, (ii) information ("B") indicating which users fulfilled which roles during that/or those procedures, and optionally (iii) information ("C") indicating which surgical procedure was performed during each of those procedures. The processor can then perform one or more of the following tasks.

1. Aggregating the information A across multiple performances of procedures (optionally procedures of the same type as indicated by information C) and comparing the aggregated data with stored data indicating a threshold level of performance. The processor can then generate a report based on the result of that comparison indicating the performance of the surgical team as a whole or of an individual in that team in comparison to the threshold. To generate a report for an individual, the processor can selectively report on those metrics indicated by the role analysis data to correspond to the role that individual took in the procedures.

2. Comparing the information A for a specific performance of a procedure with either (i) stored data indicating a threshold level of performance or (ii) aggregated information A across multiple performances of procedures (optionally procedures of the same type as indicated by information C). The processor can then generate a report based on the result of that comparison indicating the performance of the surgical team as a whole or of an individual in that team in comparison to the threshold. To generate a report for an individual, the processor can selectively report on those metrics indicated by the role analysis data to correspond to the role that individual took in the procedures.

A user may retrieve these reports from the server 28 by logging on to it using the user terminal 32.

The performance of the robotic system may be modified in dependence on the identity of a user of the system. For example, when a certain user is acting as the surgeon for a procedure, the terminal 20 may be set to pre-stored operational preferences of that user. Those preferences may previously have been defined by means of terminal 20, or another such terminal, or through an application running on the user's device 32. They may then be stored at device 32 or at server 28. The stored preferences may be transmitted to the terminal 20 and/or control unit 12 by any suitable mechanism: for example by means of a machine readable pattern displayed by device 38 and made visible to camera 25. When the user in question is acting as a surgeon, the preferences may for example include control sensitivity or the position of certain information on display 24. When the user in question is acting as a scrub nurse, the preferences may for example include which robot arm carries the endoscope. Other preferences may be set for other members of staff.

In the examples given above the system collects and distributes information regarding robotic surgical procedures. In other examples, the system could collect and distribute information on other robotic procedures such as manufacturing or mechanical repair or materials handling procedures; or on non-robotic surgical procedures.

In FIG. 1, control unit 12 and server 28 are illustrated as integrated units. In practice, their functions could be distributed between multiple devices and/or locations.

The network 27 could be a publicly accessible network such as the internet.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A surgical robotic system comprising:
a surgical robot;
a user interface console coupled to the surgical robot whereby a user can control motion of the surgical robot;
a data logger for logging data from a surgical procedure performed by means of the surgical robot; and
a portable user terminal;
the system further comprising:
a display controllable by one of the data logger and the portable user terminal, that one of the data logger and the portable user terminal being configured for displaying a machine-readable code whereby the data logger or a user of the portable user terminal can be identified; and
a camera coupled to the other of the data logger and the portable user terminal;
the said other of the data logger and the portable user terminal being configured to, on receiving from the camera an image of a machine-readable code, decode that machine-readable code to identify the data logger or a user of the portable user terminal and to cause the identified entity to be logged in association with a procedure performed by means of the surgical robot.

2. The surgical robotic system of claim 1, wherein the surgical robot comprises a robot arm having a surgical instrument attached thereto as an end effector of the robot arm.

3. The surgical robotic system of claim 1, wherein the camera is coupled to the data logger.

4. The surgical robotic system of claim 3, wherein the surgical robot is located in an operating room and the camera is positioned such that its field of view extends into the operating room.

5. The surgical robotic system of claim 3, wherein the portable user terminal is configured to locally generate the machine-readable code as a function of one or more of: an identity of a user using the portable user terminal, and a current time.

6. The surgical robotic system of claim 3, wherein the portable user terminal is configured to locally generate the machine-readable code so as to include data whereby the machine-readable code can be authenticated to the portable user terminal.

7. The surgical robotic system of claim 3, wherein the data logger is configured to, on receiving from the camera an image of a machine-readable code, determine whether that machine-readable code is authenticated to a portable user terminal and if that determination is negative to not log the identity of any user identified by the machine-readable code in association with a surgical procedure performed by means of the surgical robot.

8. The surgical robotic system of claim 3, wherein the data logger is configured to, on receiving from the camera an image of a machine-readable code, determine a time indicated by the machine-readable code and if that time is more than a predetermined time before a current time to not log the identity of any user identified by the machine-readable code in association with a surgical procedure performed by means of the surgical robot.

9. The surgical robotic system of claim 1, wherein the camera is coupled to the portable user terminal.

10. The surgical robotic system of claim 9, wherein the data logger is configured to generate the machine-readable code as a function of one or more of (i) an identity of the data logger, (ii) an identity of robotic equipment functionally coupled to the data logger, (iii) an algorithm implemented by the data logger for generating data unique to the data logger and (iv) a current time.

11. The surgical robotic system of claim 9, wherein the data logger is configured to locally generate the machine-readable code so as to include data whereby the data logger can be authenticated to the portable user terminal.

12. The surgical robotic system of claim 9, wherein the portable user terminal is configured to, on receiving from the camera an image of a machine-readable code, determine whether that machine-readable code authentically indicates a data logger and if that determination is positive to transmit data to cause the identity of a user associated with the portable user terminal to be associated with a procedure performed by means of the surgical robot.

* * * * *